United States Patent [19]
Silverman et al.

[11] Patent Number: 6,017,931
[45] Date of Patent: Jan. 25, 2000

[54] INSECTICIDAL COMPOSITIONS CONTAINING N-(SUBSTITUTED PHENYLMETHYL)-4-[BIS(SUBSTITUTED PHENYL)METHYL]PIPERIDINES

[75] Inventors: Ian R. Silverman, Moorestown; Daniel H. Cohen, Princeton; John W. Lyga, Basking Ridge, all of N.J.; Steven W. Szczepanski, Morrisville, Pa.; Syed F. Ali, Yardville, N.J.

[73] Assignee: FMC Corporation

[21] Appl. No.: 08/706,033

[22] Filed: Aug. 30, 1996

Related U.S. Application Data

[60] Continuation-in-part of application No. 08/445,315, May 19, 1995, Pat. No. 5,569,664, which is a division of application No. 08/389,675, Feb. 16, 1995, Pat. No. 5,639,763, which is a continuation-in-part of application No. 08/204,033, Mar. 1, 1994, abandoned.

[51] Int. Cl.$^7$ ...................... A61K 31/445; C07D 211/20
[52] U.S. Cl. .......................... 514/318; 514/317; 546/193; 546/236; 424/405
[58] Field of Search ..................... 546/193, 197, 546/205, 212, 214, 236; 514/317, 318, 319, 321, 326, 331; 424/405

[56] References Cited

U.S. PATENT DOCUMENTS

| | | | |
|---|---|---|---|
| 3,920,442 | 11/1975 | Albert et al. | 71/92 |
| 4,035,372 | 7/1977 | Deason | 546/229 |
| 4,628,095 | 12/1986 | Rorig et al. | 546/234 |
| 4,632,925 | 12/1986 | Mullin, Jr. et al. | 514/256 |
| 4,810,713 | 3/1989 | Yanni et al. | 514/317 |
| 5,070,087 | 12/1991 | Teng | 514/312 |
| 5,096,890 | 3/1992 | Cross et al. | 514/422 |
| 5,340,831 | 8/1994 | Cross et al. | 514/408 |
| 5,422,358 | 6/1995 | Cross | 514/320 |
| 5,569,664 | 10/1996 | Silverman et al. | 514/317 |
| 5,639,763 | 6/1997 | Silverman et al. | 514/321 |

FOREIGN PATENT DOCUMENTS

| | | |
|---|---|---|
| 183 216 | 4/1986 | European Pat. Off. . |
| 87129392 | 6/1986 | Saudi Arabia . |
| 8604552 | 12/1986 | South Africa . |
| WO 94/18172 A1 | 8/1994 | WIPO . |
| WO 95/23507 | 8/1995 | WIPO . |
| WO 96/36228 | 11/1996 | WIPO . |

OTHER PUBLICATIONS

Manoury et al., "Piperidinylalkyl benzimidazolones and quinazolinones" CA 106:5034, 1986.
Silverman et al., "Insecticidal N–substituted arylmethyl–4–bis–substituted phenyl or pyridylmethyl piperidines" CA 126:56345, 1996.
Wyngaarden et al., "Cecil textbook of medicine", 1983, p. 70.

*Primary Examiner*—Ceila Chang
*Attorney, Agent, or Firm*—FMC Corporation

[57] ABSTRACT

Compositions containing compounds of the following structure, some of which are novel, and the corresponding N-oxides and agriculturally acceptable salts, are disclosed as effective insecticides:

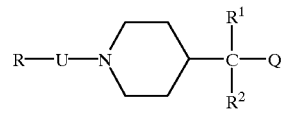

in which

U is —$(CH_2)_n$—;

Q is hydroxy;

R is

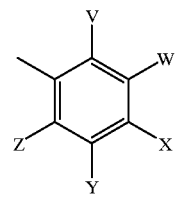

in which V, W, and Z are each hydrogen; X is selected from alkoxy, haloalkoxy, alkoxyalkyl, cycloalkylalkoxy, halocycloalkylalkoxy, alkoxycarbonyl, haloalkoxycarbonyl, cycloalkylalkoxycarbonyl, halocycloalkylalkoxycarbonyl, alkoxyalkoxycarbonyl, alkoxycarbonylamino, haloalkoxycarbonylamino, cycloalkylalkoxycarbonylamino, halocycloalkylalkoxycarbonylamino, alkylaminocarbonyl, haloalkylaminocarbonyl, cyanoalkoxycarbonylamino, phenylcarbonylamino, and phenoxycarbonyl, each cycloalkyl moiety or phenyl ring optionally substituted with halogen; Y is selected from hydrogen and halogen; n is 1, 2, or 3; $R^1$ and $R^2$ are independently selected from phenyl or pyridyl, each substituted with haloalkyl, haloalkoxy, or alkylthio; with the proviso that each aliphatic moiety contains not more than 6 carbon atoms, and halogen means bromine, chlorine or fluorine.

50 Claims, No Drawings

INSECTICIDAL COMPOSITIONS CONTAINING N-(SUBSTITUTED PHENYLMETHYL)-4-[BIS(SUBSTITUTED PHENYL)METHYL] PIPERIDINES

This is a continuation-in-part of application Ser. No. 445,315, filed May 19, 1995, now U.S. Pat. No. 5,569,664, which is a division of application Ser. No. 389,675, filed Feb. 16, 1995, now U.S. Pat. No. 5,639,763 which is a continuation-in-part of application Ser. No. 204,033, filed Mar. 1,1994, now abandoned.

The present invention relates to methods for controlling insects. In particular, it relates to control by the application of certain N-(substituted phenylmethyl)-4-[bis(substituted phenyl)methyl]piperidines to the locus where insect control is needed. While not all compounds of the class are novel, the insecticidal efficacy of these compounds is heretofore unknown It has now been found that compounds of the following structure and their corresponding N-oxides, as well as their agriculturally acceptable salts, are active as insecticides:

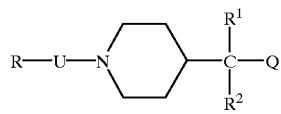

in which
U is —$(CH_2)_n$—;
Q is hydroxy;
R is

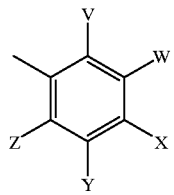

in which
V, W, and Z are each hydrogen;
X is selected from alkoxy, haloalkoxy, alkoxyalkyl, cycloalkylalkoxy, halocycloalkylalkoxy, alkoxycarbonyl, haloalkoxycarbonyl, cycloalkylalkoxycarbonyl, halocycloalkylalkoxycarbonyl, alkoxyalkoxycarbonyl, alkoxycarbonylamino, haloalkoxycarbonylamino, cycloalkylalkoxycarbonylamino, halocycloalkylalkoxycarbonylamino, alkylaminocarbonyl, haloalkylaminocarbonyl, cyanoalkoxycarbonylamino, phenylcarbonylamino, and phenoxycarbonyl, each cycloalkyl moiety or phenyl ring optionally substituted with halogen;
Y is selected from hydrogen and halogen;
n is 1, 2, or 3;
$R^1$ and $R^2$ are independently selected from phenyl or pyridyl, each substituted with haloalkyl, haloalkoxy, or alkylthio;
with the proviso that each aliphatic moiety contains not more than 6 carbon atoms, and halogen means bromine, chlorine or fluorine;
and the corresponding N-oxides and agriculturally acceptable salts.

Preferred are those compounds in which n is 1, at least one of $R^1$ and $R^2$ is phenyl substituted in the para position or 2-pyridyl substituted in the 5-position, the substituents selected from trifluoromethoxy, trifluoromethyl, and methylthio, each aliphatic moiety contains 1 to 4 carbon atoms, and halogen is fluorine;
and the corresponding N-oxides and agriculturally acceptable salts.

Particularly preferred are those compounds in which X is selected from ethoxy, propoxy, 3-fluoropropoxy, 4-fluorobutoxy, 2,2-difluorocyclopropylmethoxy, methoxycarbonyl, ethoxycarbonyl, 1-methylethoxycarbonyl, 1-fluoromethyl-2-fluoroethoxycarbonyl, cyclopropylmethoxycarbonyl, 2-methoxyethoxycarbonyl, methoxycarbonylamino, ethoxycarbonylamino, 1-methylethoxycarbonylamino, 1-methylpropoxycarbonylamino, 2-fluoroethoxycarbonylamino, 3-fluoropropoxycarbonylamino, propylaminocarbonyl, cyanomethoxycarbonylamino, 2,2-difluorocyclopropylethoxycarbonylamino, 2,4-difluorophenylcarbonylamino, and phenoxycarbonyl $R^1$ and $R^2$ are independently selected from p-trifluoromethoxyphenyl, p-trifluoromethylphenyl, and 5-trifluormethylpyrid-2-yl;
and the corresponding N-oxides and agriculturally acceptable salts. In those compounds having more than one nitrogen atom, N-oxide refers to compounds with oxygen bonded to the piperidine nitrogen.

The compounds of the present invention were prepared by methods generally known to those skilled in the art, which are described in application Ser. No. 445,315, filed May 19, 1995, now U.S. Pat. No. 5,569,664, incorporated herein by reference, and are illustrated by the following examples.

EXAMPLE 1

SYNTHESIS OF N-(4-METHOXYPHENYLMETHYL)-4-[BIS(4-TRIFLUOROMETHOXYPHENYL) HYDROXYMETHYL]PIPERIDINE (COMPOUND 1)

To a stirred mixture of 1.1 grams (0.045 gram-atom) of magnesium turnings in 30 mL of diethyl ether was added dropwise 15 mL of a solution of 11.0 grams (0.045 mole) of 4-trifluoromethoxyphenyl bromide in 30 mL of diethyl ether. Once the reaction had started, the remaining 15 mL of the bromide solution was added portionwise during a 45 minute period. When the reaction subsided, a solution of 5.0 grams (0.018 mole) of ethyl N-(4-methoxyphenylmethyl) piperidin-4-ylcarboxylate in 20 mL of diethyl ether was added dropwise during a five minute period. Upon completion of the addition, the reaction mixture was heated to reflux, where it stirred for about 30 minutes. The reaction mixture was then allowed to cool to ambient temperature, where it stirred for about 18 hours. After this time an aqueous solution saturated with ammonium chloride was added dropwise to quench the reaction. The mixture was then partitioned between water and diethyl ether. The diethyl ether layer was separated and washed first with a solution saturated with sodium chloride and then with water. The organic layer was dried with magnesium sulfate and filtered. The filtrate was concentrated under reduced pressure to a residual oil. The oil was subjected to column chromatography on silica gel, with 10% diethyl ether in hexane, 100% diethyl ether, and 10% methanol in diethyl ether as eluants.

The product-containing fractions were combined and concentrated under reduced pressure, yielding 6.7 grams of N-(4-methoxyphenylmethyl)-4-[bis(4-trifluoromethoxyphenyl)hydroxymethyl]piperidine, mp 86–96° C. The NMR spectrum was consistent with the proposed structure.

EXAMPLE 2

SYNTHESIS OF N-[2-(4-METHOXYPHENYL) ETHYL]-4-[BIS(4-TRIFLUORO) METHOXYPHENYL)HYDROXYMETHYL] PIPERIDINE (COMPOUND 2)

Step A Synthesis of ethyl N-[2-(4-methoxyphenyl)ethyl] piperidin-4-yl-carboxylate as an intermediate A stirred mixture of 5.0 grams (0.032 mole) of ethyl piperidin-4-ylcarboxylate, 5.4 grams (0.032 mole) of 1-(2-chloroethyl)-4-methoxybenzene and 4.4 grams (0.032 mole) of potassium carbonate in 50 mL of dried N,N-dimethylformamide was heated at 70° C. for about 16 hours. After this time the reaction mixture was cooled and partitioned between diethyl ether and water. The organic layer was separated and washed with water and then with an aqueous solution saturated with sodium chloride. The organic layer was dried with magnesium sulfate and filtered. The filtrate was concentrated under reduced pressure to a residue, which was subjected to column chromatography on silica gel, with diethyl ether/hexane mixtures as eluants. The product-containing fractions were combined and concentrated under reduced pressure, yielding 2.4 grams of ethyl N-[2-(4-methoxyphenyl)ethyl]piperidin-4-ylcarboxylate. The NMR spectrum was consistent with the proposed structure.

Step B Synthesis of N-[2-(4-methoxyphenyl)ethyl]-4-[bis (4-trifluoro methoxyphenyl)hydroxymethyl]piperidine (Compound 2)

This compound was prepared in a manner analogous to that of Example 1, with 1.6 grams (0.005 mole) of ethyl N-[2-(4-methoxyphenyl)ethyl]piperidin-4-ylcarboxylate, 2.4 grams (0.010 mole) of 4-trifluoromethoxyphenyl bromide, and 0.3 gram (0.011 gram-atom) of magnesium turnings in about 35 mL of diethyl ether as reagents. This reaction differed from Example 1 in that once the Grignard reaction commenced, the ethyl N-[2-(4-methoxyphenyl) ethyl]piperidin-4-ylcarboxylate was added to the diethyl ether solution of 4-trifluoromethoxyphenyl bromide. The combination was then added dropwise to the reaction mixture, thereby introducing the piperidin-4-ylcarboxylate to the reaction mixture as the Grignard reagent was forming. Upon completion of the addition the reaction mixture was stirred at ambient temperature for about 18 hours After this time an aqueous solution saturated with ammonium chloride was added dropwise to quench the reaction. The reaction mixture was then extracted with methylene chloride. The combined extracts were washed with a dilute aqueous solution of hydrochloric acid and then with an aqueous solution saturated with sodium chloride. The organic layer was dried with magnesium sulfate and filtered. The filtrate was concentrated under reduced pressure to a residue, which was subjected to column chromatography on silica gel, with hexane/diethyl ether and ethyl acetate/methanol combinations as eluants. A second column chromatography on silica gel was required, with diethyl ether as the eluant, to afford pure product. The product-containing fractions were combined and concentrated under reduced pressure, yielding 0.3 gram of N-[2-(4-methoxyphenyl)ethyl]-4-[bis(4-trifluoromethoxyphenyl)hydroxymethyl]piperidine. The NMR spectrum was consistent with the proposed structure.

EXAMPLE 3

SYNTHESIS OF N-[4-(METHYLCARBONYLAMINO) PHENYLMETHYL]4-[BIS(4-TRIFLUOROMETHOXYPHENYL) HYDROXYMETHYL]PIPERIDINE (COMPOUND 3)

Step A Synthesis N-phenylmethyl-4-[bis(4-trifluoromethoxyphenyl)hydroxymethyl]piperidine as an intermediate This compound was prepared in a manner analogous to that of Step B of Example 2, with 6.0 grams (0.024 mole) of ethyl N-phenylmethylpiperidin-4-ylcarboxylate, 1.8 grams (0.073 gram-atom) of magnesium turnings, and 17.5 grams (0.073 mole) of 4-trifluoromethoxyphenyl bromide in about 80 mL of tetrahydrofuran as reagents. The yield of N-phenylmethyl-4-[bis(4-trifluoromethoxyphenyl) hydroxymethyl]piperidine was 9.7 grams. The NMR spectrum was consistent with the proposed structure.

Step B Synthesis N-phenylmethyl-4-[bis(4-trifluoromethoxyphenyl)hydroxymethyl]piperidine hydrochloride as an intermediate A stirred solution of 1.0 gram (0.002 mole) of N-phenylmethyl-4-[bis(4-trifluoromethoxyphenyl) hydroxymethyl]piperidine in 30 mL of diethyl ether was cooled to 0° C., and hydrogen chloride gas was bubbled in. An oily solid precipitate formed. Upon completion of precipitation, the reaction mixture was taken up in 25 mL of hexane and stored in a refrigerator for about 18 hours. After this time the supernatant liquid was decanted from the precipitate. The precipitate was then stirred with about 20 mL of diethyl ether, and the mixture was concentrated under reduced pressure to a residue. The solid residue was stirred with about 20 mL of hexane, which was then decanted from the solid. The solid was dried under reduced pressure, yielding 0.8 gram of N-phenylmethyl-4-[bis(4-trifluoromethoxyphenyl)hydroxymethyl]piperidine hydrochloride. The NMR spectrum was consistent with the proposed structure.

Step C Synthesis 4-[bis(4-trifluoromethoxyphenyl) hydroxymethyl]piperidine as an intermediate Under a nitrogen atmosphere, 0.8 gram of 10% palladium on charcoal (catalyst) was placed in the reaction vessel. To this were cautiously added 25 mL of nitrogen-purged methanol, a solution of 0.8 gram (0.001 mole) of N-phenylmethyl-4-[bis(4-trifluoromethoxyphenyl) hydroxymethyl]piperidine hydrochloride in 10 mL of methanol, and then 0.9 gram (0.010 mole) of ammonium formate. Upon completion of addition, the reaction mixture was heated at reflux for about 45 minutes. The reaction mixture was then cooled to ambient temperature and diluted with 1:1-methylene chloride/methanol. The mixture was filtered through a pad of diatomaceous earth/fiberglass, and the filtrate was concentrated at about 30° C. under reduced pressure to a residue. The residue was taken up in about 70 mL of ice/water and made basic with aqueous 5% sodium hydroxide solution. The mixture was extracted with methylene chloride, and the extract was washed with an aqueous solution saturated with sodium chloride. The organic layer was then dried with sodium sulfate. The mixture was filtered, and the filtrate was concentrated under reduced pressure to a residue. The residue was stirred with petroleum ether, and 0.5 gram of solid 4-[bis(4-trifluoromethoxyphenyl)hydroxymethyl]piperidine was collected by filtration. The NMR spectrum was consistent with the proposed structure.

Step D Synthesis of N-[4-(methylcarbonylamino) phenylmethyl]-4-[bis(4-trifluoromethoxyphenyl) hydroxymethyl]piperidine (Compound 3)

To a stirred solution of 0.4 gram (0.0008 mole) of 4-[bis(4-trifluoromethoxyphenyl)hydroxymethyl]piperidine in 10 mL of dimethyl sulfoxide was added a mixture of 0.2 gram (0.0008 mole) of 4-(methylcarbonylamino) phenylmethyl chloride and 0.6 mL (0.003 mole) of N,N-diisopropylethylamine. Upon completion of addition, the reaction mixture was stirred at ambient temperature for about 18 hours. After this time the reaction mixture was partitioned between an aqueous solution saturated with sodium bicarbonate and ethyl acetate. The organic layer was separated and washed with an aqueous solution saturated with sodium chloride. The organic layer was then concentrated under reduced pressure to a residue, which was subjected to column chromatography on silica gel, with methylene chloride and mixtures of 10–50% acetone in methylene chloride as eluants. The product-containing fractions were combined and concentrated under reduced pressure, yielding about 0.3 gram of N-[4-(methylcarbonylamino)phenylmethyl]-4-[bis(4-trifluoromethoxyphenyl)hydroxymethyl]piperidine. The NMR spectrum was consistent with the proposed structure.

EXAMPLE 4

SYNTHESIS OF N-(4-PROPOXYPHENYLMETHYL)-4-[BIS(4-TRIFLUOROMETHYLPHENYL) HYDROXYMETHYL]PIPERIDINE (COMPOUND 8)

Step A Synthesis of 4-propoxyphenylmethyl chloride as an intermediate

A mixture of 53.8 grams (0.33 mole) of 4-propoxybenzaldehyde, 200 mL of ethanol, and 200 mL of tetrahydrofuran was stirred, and 3.3 grams (0.09 mole) of sodium borohydride was added portionwise during a 30 minute period. The reaction caused the reaction mixture temperature to rise to about 45° C. Upon completion of the addition, the reaction mixture was stirred for one hour and then poured into 500 mL of water containing 50 grams of ammonium chloride. The mixture was extracted with two 500 mL portions of diethyl ether, and the combined extracts were washed with one 500 mL portion of an aqueous solution saturated with sodium chloride. The organic layer was dried with magnesium sulfate and filtered. The filtrate was concentrated under reduced pressure, yielding 53.6 grams of white solid. The solid was dissolved in 75 mL of methylene chloride and 0.75 mL of pyridine was added. The solution was added dropwise to a cold (10° C.), stirred solution of 28 mL (0.38 mole) of thionyl chloride in 350 mL of methylene chloride. The complete addition required one hour, during which time the reaction mixture was maintained at 10° C. Upon completion of the addition, the reaction mixture was stirred for one hour and poured into a solution of 350 mL of water containing 100 mL of an aqueous solution saturated with ammonium chloride. The organic layer was washed with two 250 mL portions of an aqueous solution saturated with sodium bicarbonate, and dried with magnesium chloride. The mixture was filtered and the filtrate was concentrated under reduced pressure, yielding 56.4 grams of material. The material was distilled under reduced pressure, yielding 52.5 grams of 4-propoxyphenylmethyl chlorides bp 92° C./0.3 mm Hg.

Step B Synthesis of ethyl N-(4-propoxyphenylmethyl) piperidin-4-ylcarboxylate as an intermediate To a stirred solution of 47.5 grams (0.30 mole) of ethyl piperidin-4-ylcarboxylate in 70 mL (0.40 mole) of N,N-diisopropylethylamine was added dropwise a solution of 52.5 grams (0.29 mole) of 4-propoxyphenylmethyl chloride in 50 mL of dimethyl sulfoxide. The reaction caused the reaction mixture temperature to rise to about 35° C. Upon completion of the addition the reaction mixture was stirred for 30 minutes, warmed to 40° C., and then allowed to cool to ambient temperature After this time the reaction mixture was poured into 500 mL of aqueous 10% ammonium chloride. The mixture was extracted with three 250 mL portions of diethyl ether, and the combined extracts were washed with two 250 mL portions of an aqueous solution saturated with ammonium chloride, one 250 mL portion of water, and one 250 mL portion of an aqueous solution saturated with sodium chloride. The organic layer was dried with magnesium sulfate and filtered. The filtrate was concentrated under reduced pressure, yielding 80.0 grams of ethyl N-(4-propoxyphenylmethyl)piperidin-4-ylcarboxylate. The NMR spectrum was consistent with the proposed structure.

Step C Synthesis of N-(4-propoxyphenylmethyl)-4-[bis (trifluoromethylphenyl)hydroxymethyl]piperidine (Compound 8)

This compound was prepared in a manner analogous to that of Step B of Example 2, with 1.5 grams (0.005 mole) of ethyl N-(4-propoxyphenylmethyl)piperidin-4-ylcarboxylate, 3.4 grams (0.015 mole) of 4-trifluoromethylphenyl bromide, and 0.4 gram (0.015 gram-atom) of magnesium turnings in 15 mL of tetrahydrofuran as reagents. The crude product was subjected to column chromatography on silica gel, with 1:1 ethyl acetate heptane as the eluant. The product-containing fractions were combined and concentrated under reduced pressure, yielding 1.4 grams of N-(4-propoxyphenylmethyl)-4-[bis (trifluoromethylphenyl)hydroxymethyl]piperidine. The NMR spectrum was consistent with the proposed structure.

EXAMPLE 5

SYNTHESIS OF N-[4-(CYCLOPROPYLMETHOXY) PHENYLMETHYL]-4-[BIS(4-TRIFLUOROMETHYLPHENYL) HYDROXYMETHYL]PIPERIDINE (COMPOUND 9)

Step A Synthesis of 4-[bis(4-trifluoromethylphenyl) hydroxymethyl]piperidine as an intermediate A mixture of 10.0 grams (0.019 mole) of N-phenylmethyl-4-[bis(4-trifluoromethylphenyl) hydroxymethyl]piperidine hydrochloride (prepared as in Steps A and B of Example 3) and 3.0 grams of 5% palladium (catalyst) on charcoal in about 200 mL of 1:1 methanol:ethanol was shaken in a Parr hydrogenator for five to six hours at about 85° C., until the theoretical amount of hydrogen gas was taken up. The mixture was cooled to ambient temperature where it stood for about 18 hours. The mixture was filtered and concentrated under reduced pressure to a residue, which was stirred with ethyl acetate and an aqueous solution saturated with sodium bicarbonate until the residue dissolved. The organic layer was separated and passed through phase-separation paper to remove aqueous material. The organic layer was concentrated under reduced pressure, yielding about 7.0 grams of 4-[bis(4-trifluoromethylphenyl)hydroxymethyl]piperidine. The NMR spectrum was consistent with the proposed structure.

Step B Synthesis of N-[4-(cyclopropylmethoxy) phenylmethyl]-4-[bis(4-trifluoromethylphenyl) hydroxymethyl]piperidine (Compound 9)

This compound was prepared in a manner analogous to that of Step D of Example 3, with 0.4 gram (0.002 mole) of 4-(cyclopropylmethoxy)phenylmethyl chloride (prepared as in Step A of Example 16), 0.9 gram (0.002 mole) of 4-[bis(4-trifluoromethylphenyl)hydroxymethyl]piperidine, and 1.1 grams (0.008 mole) of N,N-diisopropylethylamine in about 30 mL of dimethyl sulfoxide as reagents The crude reaction product was subjected to column chromatography on silica gel with 1:1 heptane:methylene chloride, pure methylene chloride, 11:10 heptane:methylene chloride, and 1:10 acetone:methylene chloride used succesively as eluants. The product-containing fractions were combined and concentrated under reduced pressure, yielding 0.8 gram of N-[4-(cyclopropylmethoxy)phenylmethyl]-4-[bis(4-trifluoromethylphenyl)hydroxymethyl]piperidine. The NMR spectrum was consistent with the proposed structure.

EXAMPLE 6

SYNTHESIS OF N-[4-(METHOXYCARBONYLAMINO) PHENYLMETHYL]-4-[BIS(4-TRIFLUOROMETHOXYPHENYL) HYDROXYMETHYL]PIPERIDINE (COMPOUND 4)

Step A Synthesis of N-(4-aminophenylmethyl)-4-[bis(4-trifluoromethoxyphenyl)hydroxymethyl]piperidine as an intermediate A mixture of 2.5 grams (0.004 mole) of N-(4-nitrophenylmethyl)-4-[bis(4-trifluoromethoxyphenyl) hydroxymethyl]piperidine (prepared as described in Example 5) and 0.25 gram of platinum oxide catalyst in 40 mL of ethanol was shaken in a Parr hydrogenator until the theoretical amount of hydrogen gas was taken up. After this time the mixture was removed from the Parr hydrogenator and stirred with diatomaceous earth and methylene chloride. The mixture was filtered through a fiberglass filter paper. The filtrate was concentrated under reduced pressure, yielding 2.5 grams of N-(4-aminophenylmethyl)-4-[bis(4-trifluoromethoxyphenyl)hydroxymethyl]piperidine. The NMR spectrum was consistent with the proposed structure.

Step B Synthesis of N-[4-(methoxycarbonylamino) phenylmethyl]-4-[bis(4-trifluoromethoxyphenyl) hydroxymethyl]piperidine (Compound 4)

A stirred solution of 0.8 gram (0.0014 mole) of N-(4-aminophenylmethyl)-4-[bis(4-trifluoromethoxyphenyl) hydroxymethyl]piperidine in 15 mL of tetrahydrofuran was cooled to 0° C., and 0.11 mL of methyl chloroformate was added dropwise from a syringe. Upon completion of the addition, 0.12 mL of pyridine was added in one portion. The reaction mixture was allowed to warm to ambient temperature where it stirred for about 18 hours. After this time the reaction mixture was poured into a mixture of ethyl acetate and an aqueous solution saturated with sodium chloride. After a period of stirring, the organic layer was separated and dried with sodium sulfate. The mixture was filtered, and the filtrate was concentrated under reduced pressure to a residual solid. The solid was subjected to column chromatography on silica gel, with pure methylene chloride, and 1:9, 1:4, 1:3, and 3:7 mixtures of acetone:methylene chloride as eluants. The product-containing fractions were combined and concentrated under reduced pressure, yielding 0.45 gram of N-[4-(methoxycarbonylamino)phenylmethyl]-4-[bis(4-trifluoromethoxyphenyl)hydroxymethyl] piperidine. The NMR spectrum was consistent with the proposed structure.

EXAMPLE 7

SYNTHESIS OF N-[4-(METHOXYCARBONYLAMINO) PHENYLMETHYL]-4-[BIS(4-TRIFLUOROMETHOXYPHENYL) HYDROXYMETHYL]PIPERIDINE, N-OXIDE (COMPOUND 5)

To a stirred solution of 0.36 gram (0.0006 mole) of N-[4-(methoxycarbonylamino)phenylmethyl]-4-[bis(4-trifluoromethoxyphenyl)hydroxymethyl]-piperidine (prepared in Example 6) in 5 mL of chloroform is added 0.22 gram (0.0006 mole) of 50–60% 3-chloroperoxybenzoic acid. The reaction mixture is stirred for about 2 hours, after which it is washed, first, with an aqueous solution saturated with sodium bicarbonate, and then with an aqueous solution saturated with sodium chloride. The organic layer is dried over magnesium sulfate and filtered. The filtrate is concentrated under reduced pressure to a residue that is purified by preparative thin layer chromatography with 15% methanol in chloroform as the eluant. The product-containing fractions yield N-[4-(methoxycarbonylamino)phenylmethyl]-4-[bis(4-trifluoromethoxyphenyl)hydroxymethyl]piperidine, N-oxide.

Representative compounds prepared by the methods exemplified above are listed in Table 1. Characterizing properties are given in Table 2.

Biological Data

Candidate insecticides were incorporated into an artificial diet for evaluation of insecticidal activity against the tobacco budworm (*Heliothis virescens* [Fabricius]) in the following manner. Stock solutions of test chemical in dimethyl sulfoxide, ranging from 50 micromolar to 0.005 micromolar, were prepared for each rate of application. One hundred microliters of each of the stock solutions was manually stirred into 50 mL of a molten (65–70° C.) wheat germ-based artificial diet. The 50 mL of molten diet containing the test chemical was poured evenly into twenty wells in the outer two rows on each side of a twenty-five well, five row plastic tray. (Each well in the tray was about 1 cm in depth, with an opening of 3 cm by 4 cm at the lip.) Molten diet containing only dimethyl sulfoxide at the levels used in the test chemical-treated diet was poured into the five wells in the third (center) row of the tray. Each tray therefore contained one test chemical at a single rate of application, together with an untreated control. The rates of application, expressed as the negative log of the molar concentration, and the corresponding concentrations of the stock solution prepared for each rate are shown below:

| Stock Solution | Rate of Application |
| --- | --- |
| 50 micromolar | 4 |
| 5 | 5 |
| 0.5 | 6 |
| 0.05 | 7 |
| 0.005 | 8 |

Single second instar tobacco budworm larvae, selected at a stage of growth at which they uniformly weigh about 5 mg each, were placed in each well. Upon completion of infestation, a sheet of clear plastic was heat-sealed over the top of the tray by use of a common household flat iron. The trays were held at 25° C. at 60% relative humidity for five days in a growth chamber. Lighting was set at 14 hours of light and 10 hours of darkness. After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pl_{50}$) was determined by linear regression, when possible, for each test chemical. Also, where possible, the negative log of the concentration of the test chemical that provided 50% mortality ($pLC_{50}$) was determined.

Candidate insecticides with high $pl_{50}$ values from the diet test were tested for insecticidal activity in foliar evaluations against tobacco budworm, beet armyworm (*Spodoptera exigua* [Hubner]), and cabbage looper (*Trichoplusia ni* [Hubner]).

In these tests against tobacco budworm and beet armyworm, nine-day-old chick pea plants (*Cicer arietinum*) were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethoxyethanol in distilled water. Four replicates, each containing one chick pea plant, for each rate of application of test chemical were sprayed. The treated plants were transferred to a hood, where they were kept until the spray had dried.

The four chick pea plants for each replicate treated with test chemical as described above were removed from their pots by cutting the stems just above the soil line. The excised leaves and stems from the four plants in each replicate were placed in individual 8-ounce paper cups, each containing a moistened filter paper. Five second-instar (6 days old) tobacco budworms or beet armyworms (7–8 days old) were counted into each cup, taking care not to cause injury. An opaque plastic lid was placed on each cup, which was then held in a growth chamber for a 96 hour exposure period at 25° C. and 50% relative humidity. At the end of the 96 hour exposure period the cups were opened, and the numbers of dead, moribund, and live insects were counted. Using the insect counts, the efficacy of the test chemical was expressed in percent control. Percent control is derived from the total number of dead insects (TD) plus the total number of moribund insects (TM) as compared to the total number of insects (TI) in the test:

$$\% \text{ Control} = \frac{TD + TM}{TI} \times 100$$

The condition of the test plants was also observed for phytotoxicity and for reduction of feeding damage as compared to an untreated control.

Foliar tests with cabbage looper were conducted in the same manner as described above, the difference being that pinto bean plants (*Phaseolus vulgaris*) were used in place of chick pea plants.

The compounds of the present invention were active in the diet test against the tobacco budworm. In Table 3, which gives the insecticidal activity data for compounds tested in the diet test, the vast majority of the compounds exhibited $pl_{50}$ values of 6.0 or greater.

The compounds of the present invention also showed good to excellent insecticidal activity in the foliar test against tobacco budworm, beet armyworm, and cabbage looper. It can be seen from Table 4 that many compounds provided 100% control of one or more of the test insect species at an application rate of 100 ppm in the foliar test.

For insecticidal application, the active compounds are formulated into insecticidal compositions by admixture in insecticidally effective amount with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present insecticidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These insecticidal compositions may be applied either as water-diluted sprays, or dusts, or granules to the areas in which insect control is desired. These formulations may contain as little as 0.1%, 0.2% or 0.5% to as much as 95% or more by weight of active ingredient.

Dusts are free flowing admixtures of the active ingredients with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the insecticidal compound and 99.0 parts of talc.

Wettable powders are in the form of finely divided particles which disperse readily in water or other dispersant. The wettable powder is ultimately applied to the locus where insect control is desired either as a dry dust or as an emulsion in water or other liquid. Typical carriers for wettable powders include Fuller's earth, kaolin clays, silicas, and other highly absorbent, readily wet, inorganic diluents. Wettable powders normally are prepared to contain about 5–80% of active ingredient, depending on the absorbency of the carrier, and usually also contain a small amount of a wetting, dispersing, or emulsifying agent to facilitate dispersion. For example, a useful wettable powder formulation contains 80.8 parts of the insecticidal compound, 17.9 parts of Palmetto clay, and 1.0 part of sodium lignosulfonate and 0.3 part of sulfonated aliphatic polyester as wetting agents.

Other useful formulations for insecticidal applications are emulsifiable concentrates (ECs) which are homogeneous liquid compositions dispersible in water or other dispersant, and may consist entirely of the insecticidal compound and a liquid or solid emulsifying agent, or may also contain a liquid carrier, such as xylene, heavy aromatic naphthas, isophorone, or other non-volatile organic solvent. For insecticidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing, or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agents, when used, normally comprise from 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as carbon dioxide, propane, or butane, may also be used. Water-soluble or water-dispersible granules are also useful formulations for insecticidal application of the present compounds. Such granular formulations are free-flowing, non-dusty, and readily water-soluble or water-miscible. The soluble or dispersible granular formulations described in U.S. Pat. No. 3,920,442 are useful herein with the present insecticidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active insecticidal compounds of this invention may be formulated and/or applied with other insecticides, fungicides, nematicides, plant growth regulators, fertilizers, or other agricultural chemicals. In using an active compound of this invention, whether formulated alone or with other agricultural chemicals, to control insects, an effective amount and concentration of the active compound is applied to the locus where control is desired. The locus may be, e.g., the insects themselves, plants upon which the insects feed, or the insect habitat. When the locus is the soil, e.g., soil in which agricultural crops have been or will be planted, the composition of the active compound may be applied to and optionally incorporated into the soil. For most applications the effective amount may be as low as, e.g. about 10 to 500 g/ha, preferably about 100 to 250 g/ha.

It is apparent that various modifications may be made in the formulation and application of the compounds of this invention without departing from the inventive concepts herein as defined inventive concepts herein as defined in the claims.

TABLE 1

Insecticidal N-(substituted alkyl)-4-[di(substituted)hydroxymethyl]piperidines

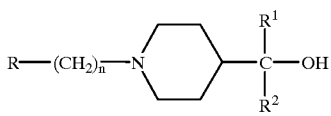

| where n is 1, and R is | and | $R^1$ and $R^2$ are |
|---|---|---|

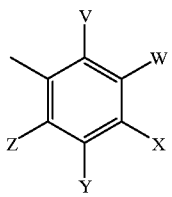            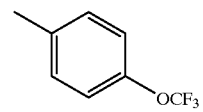

| Cmpd.No. | V | W | X | Y | Z |
|---|---|---|---|---|---|
| 1 | H | H | —OCH$_3$ | H | H |
| 2 | H | H | —OCH$_3$ | H | H |
| 3 | H | H | —NH(C=O)CH$_3$ | H | H |
| 4 | H | H | —NHCO$_2$CH$_3$ | H | H |
| 5 | H | H | —NHCO$_2$CH$_3$ N-oxide | H | H |
| 6 | H | H | —CH$_2$CH$_2$OCH$_3$ | H | H |
| 7 | H | H | —NHCO$_2$CH(CH$_3$)$_2$ N-oxide | H | H |

| R is | and | $R^1$ and $R^2$ are |
|---|---|---|

TABLE 1-continued

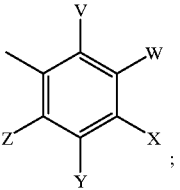

where V, W, Y, and Z are hydrogen

| Cmpd. No. | X | Cmpd. No. | X |
|---|---|---|---|
| 8 | —OC$_3$H$_7$ | 9 | 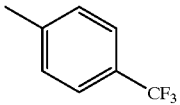 |
| 10 | —OC$_2$H$_4$CH$_2$F | 11 | —OC$_3$H$_6$CH$_2$F |
| 12 | 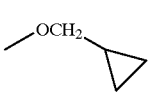 | 13 | —(C═O)OC$_2$H$_5$ |
| 14 | —(C═O)OC$_2$H$_5$<br>N-oxide | 15 | —(C═O)NHC$_3$H$_7$ |
| 16 | <br>N-oxide | 17 | —NHCO$_2$C$_2$H$_5$ |
| 18 | —NHCO$_2$C$_2$H$_5$<br>N-oxide | 19 | —NHCO$_2$CH(CH$_3$)$_2$ |
| 20 | —NHCO$_2$C(CH$_3$)$_3$ | 21 | —NHCO$_2$C(CH$_3$)$_3$<br>N-oxide |
| 22 | 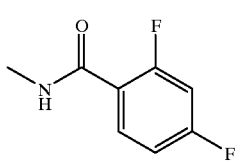 | 23 | 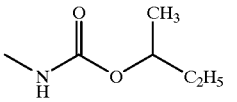<br>N-oxide |
| 24 | 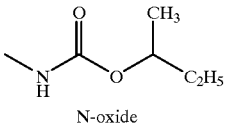<br>S-(+)-enantiomer | 25 | —NHCO$_2$C$_2$H$_4$F |
| 26 | —NHCO$_2$C$_3$H$_6$F | 27 | 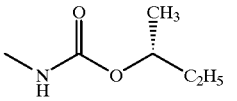 |
| 28 | —NHCO$_2$CH$_2$C≡N | 29 | —NHCO$_2$CH$_2$C≡N<br>N-oxide |
| 30 | —CO$_2$CH(CH$_3$)$_2$<br>N-oxide | 31 | —CO$_2$CH(CH$_2$F)$_2$ |
| 32 | —CO$_2$CH(CH$_2$F)$_2$<br>N-oxide | 33 | —CO$_2$CH(CH$_3$)CH$_2$OCH$_3$ |

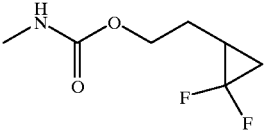

TABLE 1-continued

| 34 | [acetic acid cyclopropylmethyl ester structure] | 35 | [phenyl acetate structure] |
| --- | --- | --- | --- |
| 36 | [phenyl acetate structure] N-oxide | | |

R is

[phenyl ring with substituents V, W, X, Y, Z];

and R¹ and R² are

[p-CF₃-phenyl group]

| Cmpd.No. | V | W | X | Y | Z |
| --- | --- | --- | --- | --- | --- |
| 37 | H | H | —OC₂H₅ | F | H |
| 38 | H | H | —OC₂H₅ N-oxide | F | H |

R is

[phenyl ring with substituents V, W, X, Y, Z]

where V, W, Y and Z are hydrogen

| Cmpd. No. | X | R¹ | R² |
| --- | --- | --- | --- |
| 39 | —OC₃H₇ | [p-CF₃-phenyl] | [p-SCH₃-phenyl] |
| 40 | —OC₃H₇ | [p-CF₃-phenyl] | [2-methyl-5-CF₃-pyridyl] |
| 41 | —OC₃H₇ | [2-methyl-5-CF₃-pyridyl] | [2-methyl-5-CF₃-pyridyl] |

TABLE 2

Characterizing Data

| | |
|---|---|
| 1 | 86–96° C. |
| 2 | gel |
| 3 | oil |
| 4 | glassy solid |
| 5 | 178–182° C. |
| 6 | oil |
| 7 | 209–211° C. |
| 8 | foam |
| 9 | gummy solid |
| 10 | liquid |
| 11 | liquid |
| 12 | oil |
| 13 | 62–64° C. |
| 14 | 204–205° C. |
| 15 | 149–151° C. |
| 16 | 197–200° C. |
| 17 | 90–98° C. |
| 18 | oil |
| 19 | 210–212° C. |
| 20 | 95–100°C. |
| 21 | 180–185° C. |
| 22 | 70–75° C. |
| 23 | 204–205° C. |
| 24 | 86–89° C. |
| 25 | liquid |
| 26 | 145–148° C. |
| 27 | 160–163° C. |
| 28 | 75–82° C. |
| 29 | 189–195° C. |
| 30 | 204–205° C. |
| 31 | 129–131° C. |
| 32 | 201–203° C. |
| 33 | clear oil |
| 34 | 64–66° C. |
| 35 | 82–85° C. |
| 36 | 145–150° C. |
| 37 | 65–80° C. |
| 38 | 204–208° C. |
| 39 | oil |
| 40 | 63–68° C. |
| 41 | liquid |

TABLE 3

Insecticidal Activity When Incorporated into the Diet of Tobacco Budworm

| Cmpd. No. | Rate of Application[1] | Percent Growth Inhibition[2,3] | pI$_{50}$[4] | Percent Mortality[5] | pLC$_{50}$[6] |
|---|---|---|---|---|---|
| 1 | 4 | 100[a] | 6.1[a] | 100[a] | 4.6[a] |
| 2 | 4 | 98 | 5.6 | 25 | <4.0 |
| 3 | 4 | 95 | 4.7 | 0 | — |
| 4 | 4 | 100 | 6.8[b] | 100 | 5.5[b] |
| 5 | 5 | 100 | 6.3 | 100 | 5.9 |
| 6 | 4 | 100 | 6.1 | 100 | 4.6 |
| 7 | 4 | 100 | 6.5 | 100 | 6.0 |
| 8 | 4 | 100 | >6.0 | 100 | 5.5 |
| 9 | 4 | 100 | — | 100 | 5.6 |
| 10 | 4 | 100 | 6.6 | 100 | 5.5 |
| 11 | 4 | 100 | 6.6 | 100 | 5.1 |
| 12 | 4 | 100 | 6.1 | 100 | 5.1 |
| 13 | 4 | 100 | 6.4 | 100 | 5.9 |
| 14 | 4 | 100 | 6.5 | 100 | 5.5 |
| 15 | 4 | 100 | 6.0 | 100 | 4.6 |
| 16 | 4 | 100 | 6.1 | 100 | 5.2 |
| 17 | 4 | 100 | 6.5 | 100 | 5.6 |
| 19 | 4 | 100 | >6.0 | 100 | 5.6 |
| 20 | 4 | 100 | 6.2 | 100 | 5.6 |
| 21 | 4 | 100 | 6.2 | 100 | 5.6 |
| 22 | 4 | 100 | 6.5 | 100 | 5.9 |
| 23 | 4 | 100 | 4.6 | 95 | 4.5 |
| 24 | 4 | 100 | 6.2 | 100 | 5.5 |
| 25 | 4 | 100 | 6.0 | 100 | 5.2 |
| 26 | 4 | 100 | 6.2 | 100 | 5.5 |
| 27 | 4 | 100 | 6.4 | 100 | 5.5 |
| 28 | 4 | 100 | 6.2 | 100 | 5.5 |
| 29 | 4 | 100 | 6.1 | 100 | 5.5 |
| 30 | 4 | 100 | 6.6 | 100 | 6.4 |
| 31 | 4 | 100 | 6.1 | 100 | 5.5 |
| 32 | 4 | 100 | 6.3 | 100 | 5.9 |
| 33 | 4 | 100 | 6.3 | 100 | 5.4 |
| 34 | 4 | 100 | 6.1 | 100 | 5.4 |
| 35 | 4 | 100 | 6.0 | 100 | 5.4 |
| 36 | 4 | 100 | 6.0 | 100 | 5.4 |
| 37 | 4 | 100 | 6.2 | 100 | 5.2 |
| 38 | 4 | 100 | 6.0 | 100 | 4.9 |
| 39 | 4 | 100 | 6.0 | 100 | 4.6 |
| 40 | 4 | 100 | 6.7 | 100 | 5.6 |
| 41 | 4 | 100 | 6.5 | 100 | 5.9 |

Footnotes

[1]The rate of application is expressed as the negative log of the molar concentration of the test compound in the diet.

[2]Percent growth inhibition is derived from the total weight of the insects (IW) at each rate of application in the test relative to the total weight of insects in an untreated control, % Gr. Inh. = [IW (control) − IW (test)/IW (control)] × 100

[3]A minus % growth inhibition indicates that the insects weighed more at the termination of the test than those in the untreated control.

[4]pI$_{50}$ is the negative log of the concentration of the test chemical that provides 50% growth inhibition in the test insects.

[5]Percent mortality is derived from the number of dead insects (TD) relative to the total number of insects (TI) used in the test, $$\% \text{ Mortality} = \frac{TD}{TI} \times 100$$

[6]pLC$_{50}$ is the negative log of the concentration of the test chemical that provides 50% mortality of the test insects.

[a]Average of 3 tests.
[b]Average of 2 tests.

TABLE 4

Insecticidal Activity When Applied as Foliar Sprays

| | Rate of Application | Percent Control[1] | | |
|---|---|---|---|---|
| Cmpd No. | (ppm) | TBW[2] | CL[3] | BAW[4] |
| 1 | 100 | 80 | 100 | 55 |
| 4 | 100 | 100* | 100 | 100* |
| 5 | 100 | 100* | 100* | 100* |
| 7 | 100 | 100 | 100 | 100 |
| 10 | 100 | 100 | 100 | 100 |
| 17 | 100* | 100* | 100* | 100* |
| 19 | 100* | 100* | 100* | 100* |
| 20 | 100 | 100 | 100 | 100 |
| 21 | 100 | 100 | 100 | 100 |
| 22 | 100 | 100 | 100 | 100 |
| 25 | 100 | 87.5* | 100 | 100 |

TABLE 4-continued

Insecticidal Activity When
Applied as Foliar Sprays

| Cmpd No. | Rate of Application (ppm) | Percent Control[1] | | |
|---|---|---|---|---|
| | | TBW[2] | CL[3] | BAW[4] |
| 27 | 100 | 100 | 89? | 95 |
| 40 | 100 | 100 | 100 | 100 |

[1]Percent control is derived from the total number of dead insects (TD) plus the total number of moribund insects (TM) as compared to the total number of insects (TI) in the test:
$$\% \text{ Control} = \frac{TD + TM}{TI} \times 100$$

[2]TBW is tobacco budworm (*Heliothis virescens*[Fabricius])
[3]CL is cabbage looper (*Trichoplusia ni*[Hubner])
[4]BAW is beet armyworm (*Spodoptera exigua*[Hubner])
*indicates an average of more than one test.

We claim:
1. A compound of the formula:

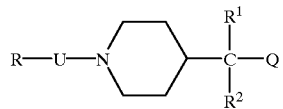

in which
U is —(CH$_2$)$_n$—;
Q is hydroxy;
R is

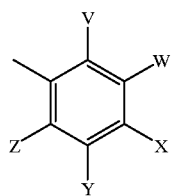

in which
V, W and Z are each hydrogen;
X is selected from alkoxy, haloalkoxy, alkoxyalkyl, cycloalkylalkoxy, halocycloalkylalkoxy, alkoxycarbonyl, haloalkoxycarbonyl, cycloalkylalkoxycarbonyl, halocycloalkylalkoxycarbonyl, alkoxyalkoxycarbonyl, alkoxycarbonylamino, haloalkoxycarbonylamino, cycloalkylalkoxycarbonylamino, halocycloalkylalkoxycarbonylamino, alkylaminocarbonyl, haloalkylaminocarbonyl, cyanoalkoxycarbonylamino, phenylcarbonylamino, phenoxycarbonyl, and phenoxycarbonyl, each cycloalkyl moiety or phenyl ring optionally substituted with halogen;
Y is selected from hydrogen and halogen;
n is 1, 2, or 3;
R$^1$ and R$^2$ are independently selected from phenyl or pyridyl, each substituted with haloalkyl, haloalkoxy, or alkylthio;
with the proviso that at least one of R$^1$ and R$^2$ is a substituted pyridyl, each aliphatic moiety contains not more than 6 carbon atoms, and halogen means bromine, chlorine or fluorine;
and the corresponding N-oxides and agriculturally acceptable salts.

2. A compound of claim 1 in which n is 1, at least one of R$^1$ and R$^2$ is phenyl substituted in the para position or 2-pyridyl substituted in the 5-position, the substituents selected from trifluoromethoxy, trifluoromethyl, and methylthio, each aliphatic moiety contains 1 to 4 carbon atoms, and halogen is fluorine;
and the corresponding N-oxides and agriculturally acceptable salts.

3. A compound of claim 2 in which X is selected from ethoxy, propoxy, 3-fluoropropoxy, 4-fluorobutoxy, 2,2-difluorocyclopropylmethoxy, methoxycarbonyl, ethoxycarbonyl, 1-methylethoxycarbonyl, 1-fluoromethyl-2-fluoroethoxycarbonyl, cyclopropylmethoxycarbonyl, 2-methoxyethoxycarbonyl, methoxycarbonylamino, ethoxycarbonylamino, 1-methylethoxycarbonylamino, 1-methylpropoxycarbonylamino, 2-fluoroethoxycarbonylamino, 3-fluoropropoxycarbonylamino, propylaminocarbonyl, cyanomethoxycarbonylamino, 2-(2,2-difluorocyclopropyl)ethoxycarbonylamino, 2,4-difluorophenylcarbonylamino, and phenoxycarbonyl;
R$^1$ and R$^2$ are independently selected from p-trifluoromethoxyphenyl, p-trifluoromethylphenyl, and 5-trifluormethylpyrid-2-yl;
and the corresponding N-oxides and agriculturally acceptable salts.

4. A compound of claim 3 in which X is propoxy, and Y is hydrogen.

5. The compound of claim 4 in which R$^1$ and R$^2$ are each 5-trifluormethylpyrid-2-yl.

6. The compound of claim 4 in which R$^1$ is p-trifluoromethylphenyl and R$^2$ is 5-trifluormethylpyrid-2-yl.

7. A compound of the formula:

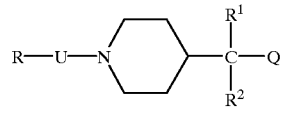

in which
U is —(CH$_2$)$_n$—;
Q is hydroxy;
R is

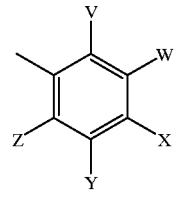

in which
V, W, and Z are each hydrogen;
X is selected from alkoxy, haloalkoxy, alkoxyalkyl, cycloalkylalkoxy, halocycloalkylalkoxy, alkoxycarbonyl, haloalkoxycarbonyl, cycloalkylalkoxycarbonyl, halocycloalkylalkoxycarbonyl, alkoxyalkoxycarbonyl, alkoxycarbonylamino, haloalkoxycarbonylamino, cycloalkylalkoxycarbonylamino, halocycloalkylalkoxycarbonylamino, alkylaminocarbonyl, haloalkylaminocarbonyl, cyanoalkoxycarbonylamino, phenylcarbonylamino, and phenoxycarbonyl, each cycloalkyl moiety or phenyl ring optionally substituted with halogen;

Y is selected from hydrogen and halogen;

n is 1, 2, or 3;

$R^1$ and $R^2$ are independently selected from phenyl substituted with haloalkyl, haloalkoxy, or alkylthio;

with the proviso that at least one of $R^1$ and $R^2$ is haloalkoxyphenyl, each aliphatic moiety contains not more than 6 carbon atoms, and halogen means bromine, chlorine or fluorine;

and the corresponding N-oxides and agriculturally acceptable salts.

8. A compound of claim 7 in which n is 1, at least one of $R^1$ and $R^2$ is phenyl substituted in the para position, the substituents selected from trifluoromethoxy, trifluoromethyl, and methylthio, each aliphatic moiety contains 1 to 4 carbon atoms, and halogen is fluorine;

and the corresponding N-oxides and agriculturally acceptable salts.

9. A compound of claim 8 in which X is selected from ethoxy, propoxy, 3-fluoropropoxy, 4-fluorobutoxy, 2,2-difluorocyclopropylmethoxy, methoxycarbonyl, ethoxycarbonyl, 1-methylethoxycarbonyl, 1-fluoromethyl-2-fluoroethoxycarbonyl, cyclopropylmethoxycarbonyl, 2-methoxyethoxycarbonyl, methoxycarbonylamino, ethoxycarbonylamino, 1-methylethoxycarbonylamino, 1-methylpropoxycarbonylamino, 2-fluoroethoxycarbonylamino, 3-fluoropropoxycarbonylamino, propylaminocarbonyl, cyanomethoxycarbonylamino, 2-(2,2-difluorocyclopropyl)ethoxycarbonylamino, 2,4-difluorophenylcarbonylamino, and phenoxycarbonyl;

$R^1$ and $R^2$ are independently selected from p-trifluoromethoxyphenyl, p-trifluoromethylphenyl, p-methylthiophenyl;

and the corresponding N-oxides and agriculturally acceptable salts.

10. A compound of claim 9 in which each of $R^1$ and $R^2$ is p-trifluoromethoxyphenyl.

11. The compound of claim 10 in which Y is hydrogen and X is 2-methoxyethyl.

12. The compound of claim 10 in which Y is hydrogen, and X is 1-methylethoxycarbonylamino, and the compound is the N-oxide.

13. A compound of the formula:

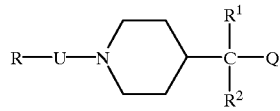

in which

U is —$(CH_2)_n$—;

Q is hydroxy;

R is

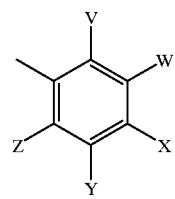

in which

V, W, and Z are each hydrogen;

X is selected from haloalkoxy, alkoxyalkyl, cycloalkylalkoxy, halocycloalkylalkoxy, haloalkoxycarbonyl, cycloalkylalkoxycarbonyl, halocycloalkylalkoxycarbonyl, alkoxyalkoxycarbonyl, haloalkoxycarbonylamino, cycloalkylalkoxycarbonylamino, halocycloalkylalkoxycarbonylamino, cyanoalkoxycarbonylamino, phenylcarbonylamino, and phenoxycarbonyl, each cycloalkyl moiety or phenyl ring optionally substituted with halogen;

Y is selected from hydrogen and halogen;

n is 1, 2, or 3;

$R^1$ and $R^2$ are independently selected from phenyl substituted with haloalkyl, haloalkoxy, or alkylthio;

with the proviso that each aliphatic moiety contains not more than 6 carbon atoms, and halogen means bromine, chlorine or fluorine;

and the corresponding N-oxides and agriculturally acceptable salts.

14. A compound of claim 13 in which n is 1, at least one of $R^1$ and $R^2$ is phenyl substituted in the para position, the substituents selected from trifluoromethoxy, trifluoromethyl, and methylthio, each aliphatic moiety contains 1 to 4 carbon atoms, and halogen is fluorine.

15. A compound of claim 14 in which X is selected from 3-fluoropropoxy, 4-fluorobutoxy, 2,2-difluorocyclopropylmethoxy, 1-fluoromethyl-2-fluoroethoxycarbonyl, cyclopropylmethoxycarbonyl, 2-fluoroethoxycarbonylamino, 3-fluoropropoxycarbonylamino, cyanomethoxycarbonylamino, and 2-(2,2-difluorocyclopropyl)ethoxycarbonylamino;

$R^1$ and $R^2$ are independently selected from p-trifluoromethoxyphenyl, p-trifluoromethylphenyl, p-methylthiophenyl;

and the corresponding N-oxides and agriculturally acceptable salts.

16. The compound of claim 15 in which Y is hydrogen and X is 3-fluoropropoxy.

17. The compound of claim 15 in which Y is hydrogen and X is 4-fluorobutoxy.

18. The compound of claim 15 in which Y is hydrogen and X is 2,2-difluorocyclopropylmethoxy.

19. The compound of claim 15 in which Y is hydrogen and X is 1-fluoromethyl-2-fluoroethoxy.

20. The compound of claim 15 in which Y is hydrogen, X is 1-fluoromethyl-2-fluoroethoxy, and the compound is the N-oxide.

21. The compound of claim 15 in which Y is hydrogen and X is cyclopropylmethoxycarbonyl.

22. The compound of claim 15 in which Y is hydrogen and X is 2-methoxyethoxycarbonyl.

23. The compound of claim 15 in which Y is hydrogen and X is 2-fluoroethoxycarbonylamino.

24. The compound of claim 15 in which Y is hydrogen and X is 3-fluoropropoxycarbonylamino.

25. The compound of claim 15 in which Y is hydrogen and X is cyanomethoxycarbonylamino.

26. The compound of claim 15 in which Y is hydrogen and X is cyanomethoxycarbonylamino, and the compound is the N-oxide.

27. The compound of claim 15 in which Y is hydrogen and X is 2-(2,2-difluorocyclopropyl)ethoxycarbonylamino.

28. A composition containing an insecticidally effective amount of a compound of the formula:

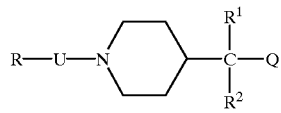

in which

U is —$(CH_2)_n$—;

Q is hydroxy;

R is

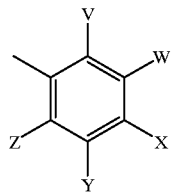

in which

V, W, and Z are each hydrogen;

X is selected from alkoxy, haloalkoxy, alkoxyalkyl, cycloalkylalkoxy, halocycloalkylalkoxy, alkoxycarbonyl, haloalkoxycarbonyl, cycloalkylalkoxycarbonyl, halocycloalkylalkoxycarbonyl, alkoxyalkoxycarbonyl, alkoxycarbonylamino, haloalkoxycarbonylamino, cycloalkylalkoxycarbonylamino, halocycloalkylalkoxycarbonylamino, alkylaminocarbonyl, haloalkylaminocarbonyl, cyanoalkoxycarbonylamino, phenylcarbonylamino, and phenoxycarbonyl, each cycloalkyl moiety or phenyl ring optionally substituted with halogen;

Y is selected from hydrogen and halogen;

n is 1, 2, or 3;

$R^1$ and $R^2$ are independently selected from phenyl or pyridyl, each substituted with haloalkyl, haloalkoxy, or alkylthio;

with the proviso that each aliphatic moiety contains not more than 6 carbon atoms, and halogen means bromine, chlorine or fluorine;

and the corresponding N-oxides and agriculturally acceptable salts; in admixture with at least one agriculturally acceptable extender or adjuvant.

29. A composition of claim 28 in which n is 1, at least one of $R^1$ and $R^2$ is phenyl substituted in the para position or 2-pyridyl substituted in the 5-position, the substituents selected from trifluoromethoxy, trifluoromethyl, and methylthio, each aliphatic moiety contains 1 to 4 carbon atoms, and halogen is fluorine;

and the corresponding N-oxides and agriculturally acceptable salts.

30. A composition of claim 29 in which X is selected from ethoxy, propoxy, 3-fluoropropoxy, 4-fluorobutoxy, 2,2-difluorocyclopropylmethoxy, methoxycarbonyl, ethoxycarbonyl, 1-methylethoxycarbonyl, 1-fluoromethyl-2-fluoroethoxycarbonyl, cyclopropylmethoxycarbonyl, 2-methoxyethoxycarbonyl, methoxycarbonylamino, ethoxycarbonylamino, 1-methylethoxycarbonylamino, 1-methylpropoxycarbonylamino, 2-fluoroethoxycarbonylamino, 3-fluoropropoxycarbonylamino, propylaminocarbonyl, cyanomethoxycarbonylamino, 2-(2,2-difluorocyclopropyl)ethoxycarbonylamino, 2,4-difluorophenylcarbonylamino, and phenoxycarbonyl; and $R^1$ and $R^2$ are independently selected from p-trifluoromethoxyphenyl, p-trifluoromethylphenyl, p-methylthiophenyl, and 5-trifluormethylpyrid-2-yl.

31. A composition of claim 30 in which $R^1$ and $R^2$ are each p-trifluoromethylphenyl.

32. A composition of claim 31 in which Y is hydrogen and X is ethoxycarbonyl.

33. The composition of claim 31 in which Y is hydrogen, X is ethoxycarbonyl, and the compound is the N-oxide.

34. A composition of claim 31 in which Y is hydrogen and X is ethoxycarbonylamino.

35. A composition of claim 31 in which Y is hydrogen, X is ethoxycarbonylamino, and the compound is the N-oxide.

36. A composition of claim 31 in which Y is hydrogen and X is 1-methylethoxycarbonylamino.

37. A composition of claim 31 in which Y is hydrogen, X is 1-methylethoxycarbonylamino, and the compound is the N-oxide.

38. A composition of claim 31 in which Y is hydrogen and X is 1,1-dimethylethoxycarbonylamino.

39. A composition of claim 31 in which Y is hydrogen, X is 1,1-dimethylethoxycarbonylamino, and the compound is the N-oxide.

40. A composition of claim 31 in which Y is hydrogen and X is 1-methylpropoxycarbonylamino.

41. A composition of claim 31 in which Y is hydrogen, X is 1-methylpropoxycarbonylamino, and the compound is the N-oxide.

42. A composition of claim 31 in which Y is hydrogen and X is 1-methylpropoxycarbonylamino, and the compound is the S-(+) enantiomer.

43. A composition of claim 31 in which Y is hydrogen and X is phenoxycarbonyl.

44. A composition of claim 31 in which Y is hydrogen, X is phenoxycarbonyl, and the compound is the N-oxide.

45. A composition of claim 31 in which Y is hydrogen and X is 2,4-difluorophenylcarbonylamino.

46. A composition of claim 31 in which Y is hydrogen and X is propylaminocarbonyl.

47. A composition of claim 30 in which Y is fluorine and X is ethoxy.

48. A composition of claim 30 in which Y is fluorine, X is ethoxy, and the compound is the N-oxide.

49. The composition of claim 30 in which Y is hydrogen, X is propoxy, $R^1$ is p-trifluoromethylphenyl, and $R^2$ is p-methylthiophenyl.

50. A method of controlling insects which comprises applying to a locus where control is desired an insecticidally effective amount of a composition of claim 28.

* * * * *